United States Patent
Hsueh et al.

(10) Patent No.: US 8,415,504 B2
(45) Date of Patent: Apr. 9, 2013

(54) CATALYST CARRIER, CATALYST THEREON AND C-C COUPLING METHOD USE THE SAME

(75) Inventors: Mao-Lin Hsueh, Hsinchu (TW);
Cheng-Wei Yeh, Hsinchu (TW);
Kuo-Chen Shih, Hsinchu (TW);
Hsiao-Chun Yeh, Hsinchu (TW);
Yi-Zhen Chen, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 135 days.

(21) Appl. No.: 12/979,037

(22) Filed: Dec. 27, 2010

(65) Prior Publication Data
US 2012/0165574 A1 Jun. 28, 2012

(30) Foreign Application Priority Data
Nov. 24, 2010 (TW) .............................. 099140505 A

(51) Int. Cl.
*C07C 45/68* (2006.01)
*C07C 41/30* (2006.01)
*C08F 292/00* (2006.01)
*B01J 31/06* (2006.01)

(52) U.S. Cl. ...................... 568/312; 568/642; 525/326.6; 502/159

(58) Field of Classification Search ................... 568/312, 568/642; 502/159; 525/326.6
See application file for complete search history.

(56) References Cited

U.S. PATENT DOCUMENTS

| | | | |
|---|---|---|---|
| 6,159,892 A | 12/2000 | Moy et al. | |
| 6,555,704 B1 | 4/2003 | Elango | |
| 6,603,013 B2 | 8/2003 | Sun et al. | |
| 7,294,679 B2 | 11/2007 | Peterson et al. | |
| 7,847,038 B2 | 12/2010 | Casty et al. | |
| 2002/0016512 A1 | 2/2002 | Sun et al. | |
| 2004/0171833 A1 | 9/2004 | Buchwald et al. | |
| 2006/0258875 A1 | 11/2006 | Reyes et al. | |
| 2008/0177112 A1 | 7/2008 | Tanaka et al. | |

FOREIGN PATENT DOCUMENTS

| | | |
|---|---|---|
| AU | 1649302 | 6/2002 |
| CN | 1686972(A) | 10/2005 |
| CN | 1990107 | 7/2007 |
| WO | WO02/48039 | 6/2002 |

OTHER PUBLICATIONS

Emily Baird Anderson, Synthesis and Non-Covalent Interactions of Novel Phosphonium-Containing Polymers, Dissertation—Aug. 18, 2010.*
Shin, J., Bertoia, J., Czerwinski, K. R., and Bae, C., "A new homogeneous polymer support based on syndiotactic polystyrene and its application in palladium-catalyzed Suzuki-Mitaura cross-cpuling reactions." Green Chem., 2009. 11. 1576-1580.
Jana, S., Haldar, S., Koner, S., "Heterogeneous Suzuki and Still coupling reactions using highly efficient palladium(0) immobilized MCM-41 catalyst," Tetrahedron Letters 50 (2009) 4820-4823.
Felix E. Coodson, Thomas I. Wallow, and Bruce M. Novak., Application of "Transfer-Free" Suzuki Coupling Protocols toward the Synthesis of "Unambiguously Linear" Poly(p-phenylenes) Macromolecules 31. 2047-2056, (1998).

* cited by examiner

*Primary Examiner* — Sikarl Witherspoon
(74) *Attorney, Agent, or Firm* — Muncy, Geissler, Olds & Lowe, PLLC

(57) ABSTRACT

The disclosure provides a catalyst carrier, including a nano carbon material; and a polymer grafted on the nano carbon material, wherein the polymer has a repetitive unit comprising a phosphorous atom. The disclosure further provides a catalyst deposited on the catalyst carrier of the disclosure. The catalyst of the disclosure has high reactivity, and is easy to be recovered in C—C coupling reactions such as a Suzuki-Miyaura coupling reaction.

18 Claims, 1 Drawing Sheet

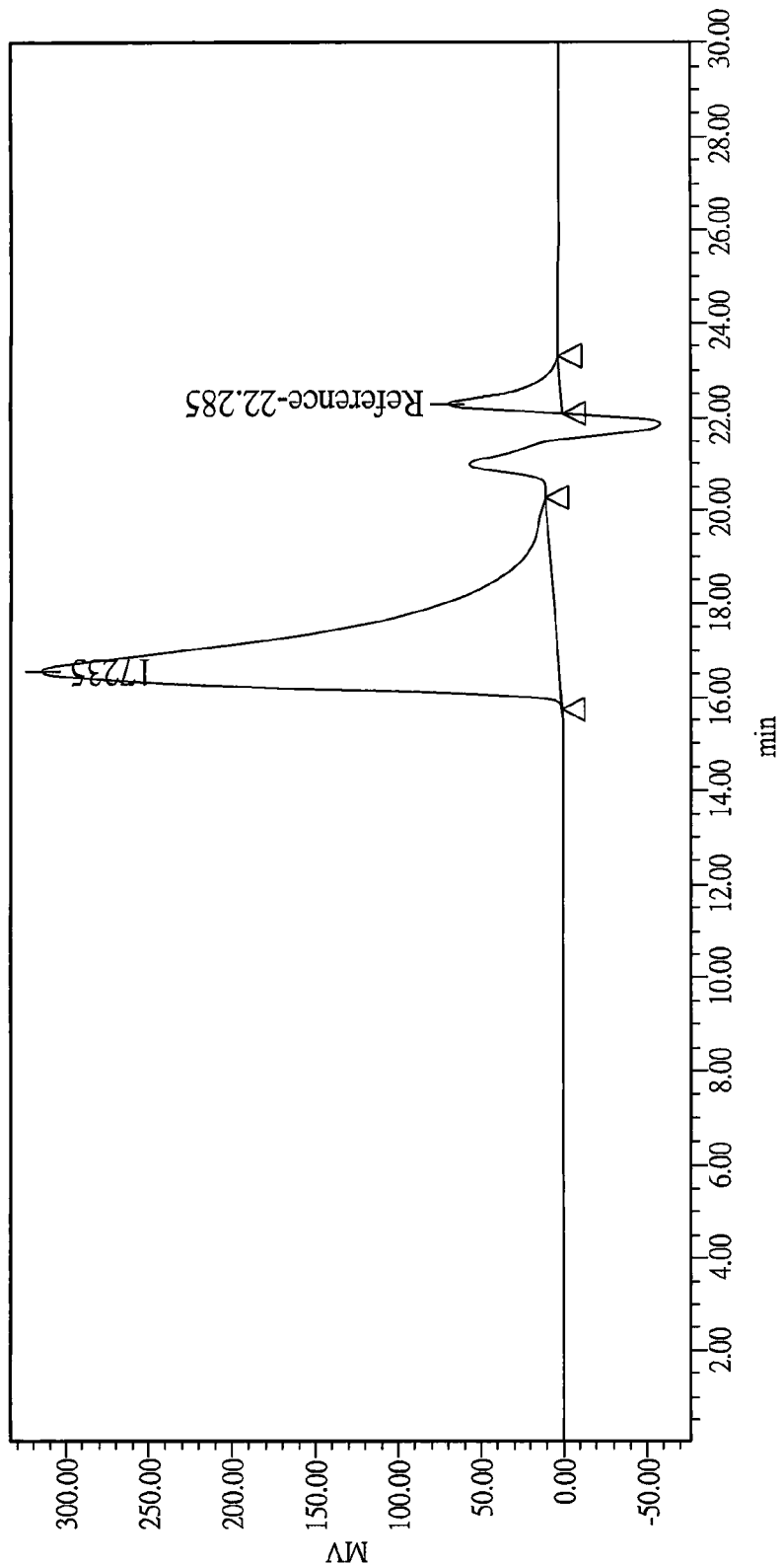

CATALYST CARRIER, CATALYST THEREON AND C-C COUPLING METHOD USE THE SAME

TECHNICAL FIELD

The disclosure relates to a catalyst carrier and a catalyst thereon, and C—C coupling method using the same.

BACKGROUND

In the chemical industry, a catalyst plays a critical role for enhancing reaction activity, reducing reaction time and reducing production cost. In general, catalysts may be classified into homogeneous catalysts and heterogeneous catalysts. Homogeneous catalysts usually have high activity and selectivity, but are not easy to be recycled, resulting in high production cost. Heterogeneous catalysts are easy to be recycled, but have lower conversion rate, poor selectivity, and need stricter reaction conditions in comparison with homogeneous catalysts.

Heterogeneous catalysts can be used in C—C coupling reactions. U.S. Pat. No. 6,603,013 discloses a C—C coupling reaction of α-bromostyrene and phenylboronic acid using a heterogeneous palladium catalyst deposited on a carbon black. This kind of heterogeneous catalyst can be easily separated out from the product, but has slower reaction rate, and may have problems of having metal ion leaching out from the carbon black. US Patent Application Publication No. 2008/177,112A discloses a palladium nano particle for catalyzing a C—C coupling reaction. However, this nano particle has slower reaction rate, thus the reaction needs to be performed at higher temperature and pressure and takes longer time to obtain a desired conversion rate.

In addition, in the chemical industry, homogeneous catalysts are also widely used. For example, CN1,686,972 discloses an organic palladium (Pd) catalyst for catalyzing a C—C coupling reaction to produce a liquid crystal compound used for TFT-LCD. The requirement of high purity liquid crystal compound demanded a costly purification process. In addition the homogeneous catalyst used cannot be recovered, resulting in high production cost.

Hence, there is still a need from the industries to develop a catalyst, which has high reactivity and being easy to be recovered.

SUMMARY

The disclosure provides a catalyst carrier, including a nano carbon material; and a polymer grafted on the nano carbon material, wherein the polymer has a repetitive unit comprising a phosphorous atom.

The disclosure further provides a catalyst deposited on the catalyst carrier of the disclosure. The catalyst of the disclosure includes a nano carbon material; a polymer grafted on the nano carbon material, wherein the polymer has a repetitive unit comprising a phosphorous atom; and a transition metal element is coordinated onto the phosphorous atom.

In the catalyst carrier and the catalyst of the disclosure, a main chain of the polymer has an end group grafted on the nano carbon material, wherein the end group of the main chain containing a carbon atom.

There are various methods such as free radical reactions, atom transfer radical polymerization (ATRP), reversible addition-fragmentation chain transfer polymerization (RAFT), ring-opening polymerization (ROP), cation/anion polymerization or condensation polymerization for grafting the polymer onto the nano carbon material. In the above-mentioned methods, the addition reaction of the nano carbon material and the polymer chain may be performed in the presence of free radicals, so as to graft the polymer on the surface of the nano carbon material. The polymer grafted on the nano carbon material may be formed by mixing the monomer, radical initiator and the nano particle.

In the catalyst carrier and the catalyst of some embodiments, the polymer has functional groups which can be coordinated onto the transition metal catalyst. In one embodiment, a reaction of the polymer and a nano carbon tube is performed to form the polymer grafted on the nano carbon tube via a radical pathway. The polymer is consisted of a repetitive unit containing a phosphorous atom. The repetitive unit has a structure of formula (I):

wherein $R_1$ and $R_2$ are independently selected from the group consisting of $C_1$-$C_{10}$alkyl, $C_3$-$C_8$cycloalkyl, $C_6$-$C_{10}$aryl, $C_1$-$C_4$alkyl or $C_2$-$C_4$alkenyl substituted $C_6$-$C_{10}$aryl and $C_6$-$C_{10}$heteroaryl; $R_3$ is one selected from the group consisting of a $C_1$-$C_{10}$alkylene, $C_3$-$C_8$cycloalkylene, $C_3$-$C_8$cycloalkylene or $C_6$-$C_{12}$arylene having a carbon atom bound to P and substituted with a hetero atom, $C_6$-$C_{12}$arylene, a halo substituted $C_6$-$C_{12}$arylene, fused $C_6$-$C_{12}$arylene, fused $C_6$-$C_{12}$arylene substituted with $C_6$-$C_{12}$aryl and, a metal complex having cyclo-olefins as ligands, in which one of the cyclo-olefins is bound to the main chain of the polymer and bound to P; P is a phosphorous; and n is a positive integer With regard to the structure of formula (I), the repetitive unit may be one of the following formulae (Ia) to (Ih):

-continued (Id)
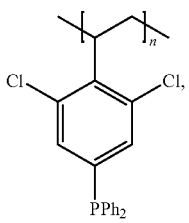

(Ie)
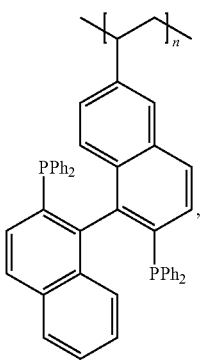

(If)
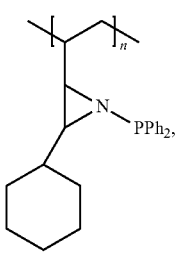

(Ig)
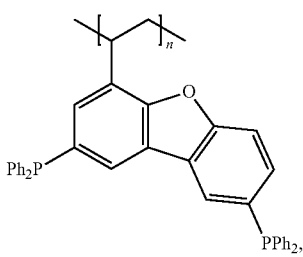

(Ih)
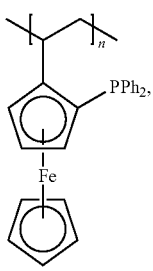

wherein Ph is phenyl, and n is a positive integer.

The polymer may further include a repetitive unit not containing a phosphorous atom. In one embodiment, the repetitive unit inert to the metal ligands is comprised of polymeric vinyl-based monomers. Specifically, the repetitive unit comprised of polymeric vinyl-based monomers has a structure of formula (II):

(II)
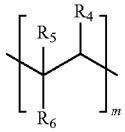

wherein $R_4$ and $R_6$ are independently selected from the group consisting of H, ester, $C_1$-$C_{10}$alkyl, $C_2$-$C_8$alkene, $C_3$-$C_8$cycloalkyl, 4- to 8-membered heterocycloalkyl and $C_6$-$C_{10}$aryl; $R_5$ is H or $C_1$-$C_{10}$alkyl; and m is a positive integer.

In the disclosure, the ratio of the phosphorous atom-containing unit is adjusted to control the amount of catalyst coordinated onto the polymer. Further, the polymer grafted on the nano carbon material, and the nano carbon material has high surface area and great mechanical strength, such that the catalyst of the disclosure is easy to be recovered. Moreover, the catalyst of the disclosure has great conversion rate and yield and significantly eliminates the leaching of the metals from the carrier, so that the amount of the metal leaching in the product is less than 5%.

BRIEF DESCRIPTION OF THE DRAWINGS

FIG. 1 shows GPC analysis of PDPVP polymer of the disclosure.

DETAILED DESCRIPTION OF THE PREFERRED EMBODIMENTS

The detailed description of the disclosure is illustrated by the following specific examples. Persons ordinarily skilled in the art can conceive the other advantages and effects of the disclosure based on the disclosure contained in the specification of the disclosure.

In the catalyst carrier and the catalyst of the disclosure, the nano carbon material is selected from the group consisting of a single-layer carbon nano-tube, a multi-layer carbon nano-tube, a nano carbon fiber, a nano carbon ball, an active carbon and a carbon black.

In the disclosure, "polymer" refers to a polymer having functional groups, wherein the functional groups of the polymer contain phosphorous atom(s) in one of the repetitive unit of the polymer. The repetitive unit of the polymer has a structure of formula (I):

(I)

wherein $R_1$ and $R_2$ are independently selected from the group consisting of $C_1$-$C_{10}$alkyl, $C_3$-$C_8$cycloalkyl, $C_6$-$C_{10}$aryl, $C_1$-$C_4$alkyl or $C_2$-$C_4$alkenyl substituted $C_6$-$C_{10}$aryl and $C_6$-$C_{10}$heteroaryl; $R_3$ is one selected from the group consisting of a $C_1$-$C_{10}$alkylene, $C_3$-$C_8$cycloalkylene, $C_3$-$C_8$cycloalkylene or $C_6$-$C_{12}$arylene having a carbon atom bound to P and substituted with a hetero atom, $C_6$-$C_{12}$arylene, a halo substituted $C_6$-$C_{12}$arylene, fused $C_6$-$C_{12}$arylene, fused $C_6$-$C_{12}$arylene substituted with $C_6$-$C_{12}$aryl, and a metal complex having cyclo-olefins as ligands, in which one of the cyclo-olefins is bound to the main chain of the polymer and bound to P; P is phosphorous; and n is a positive integer.

With regard to the structure of formula (I), the repetitive unit may be one of the following formulae (Ia) to (Ih):

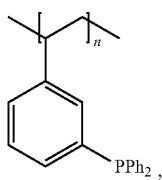
(Ia)

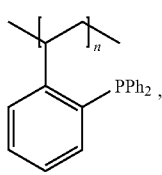
(Ib)

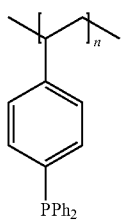
(Ic)

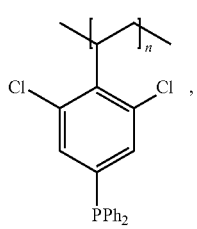
(Id)

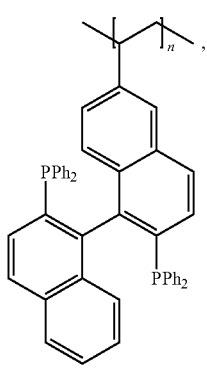
(Ie)

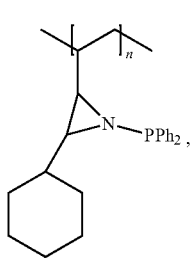
(If)

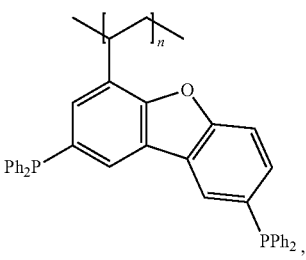
(Ig)

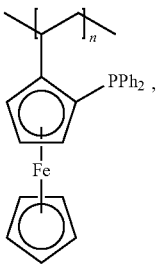
(Ih)

wherein Ph is phenyl, and n is a positive integer.

The fused $C_6$-$C_{12}$ arylene may be, but not limited to, fused to form a heterocyclic group, and the heterocyclic group may be further fused with other aryl groups. $R_3$ also could be a metal complex having cyclo-olefins as ligands, which may be a complex formed by cyclopentadiene and iron (Fe), wherein one cyclo-olefin of the metal complex is bound to the main chain of the polymer and bound to P.

The polymer may further include a repetitive unit, inert to the metal ligands, not containing a phosphorous atom. In one embodiment, the repetitive unit is comprised of polymeric vinyl-based monomers. Specifically, the repetitive unit comprised of polymeric vinyl-based monomers has a structure of formula (II):

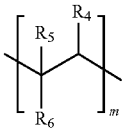
(II)

wherein $R_4$ and $R_6$ are independently selected from the group consisting of H, ester, $C_1$-$C_{10}$alkyl, $C_2$-$C_8$alkene, $C_3$-$C_8$cycloalkyl, 4- to 8-membered heterocycloalkyl and $C_6$-$C_{10}$aryl; $R_5$ is H or $C_1$-$C_{10}$alkyl; and m is a positive integer.

In the disclosure, the polymer or random copolymer may be formed by living radical polymerization methods. In one embodiment, the polymer has a structure of formula (IV):

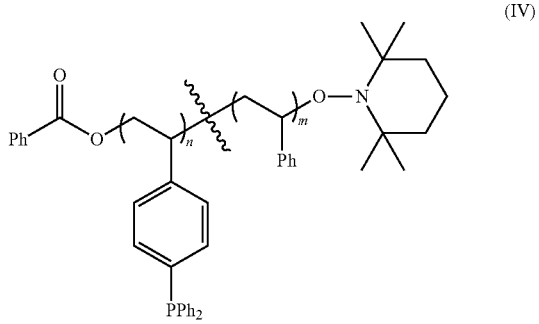

(IV)

wherein Ph is phenyl; PPh$_2$ is diphenylphosphine; and both m and n are positive integers.

When heating the polymer with nano carbon materials, the carbon oxygen bond of the polymer will cleavage to form 2,2,6,6-tetramethylpiperidine-1-oxyl and a polymer with a radical on the chain end. The polymer thus can be attached onto the nano carbon material through the radical on the chain end.

In the disclosure, the free radical initiator used for the living radical polymerization to produce the polymers is not specifically limited, and may be, but not limited to, peroxides, peroxide esters and azo compounds. In one embodiment, the free radical initiator is benzoyl peroxide (BPO). In addition, the nitroxide compound used in radical polymerization is not limited to 2,2,6,6-tetramethylpiperidine-1-oxyl (TEMPO). Included is any nitroxide compound which may be bound to the end group of the main chain, and make the chain end of the polymer to form free radicals to be bound to the nano carbon material upon thermal treatment in the grafting reaction.

In the disclosure, the grafting reactions of the polymers onto the nano carbon materials are not specifically limited. The polymer grafted onto the nano carbon material may be obtained by the free radical reaction of the nano carbon material and the polymer containing a fragment of 2,2,6,6-tetramethylpiperidine-1-oxyl, or by the reaction of the nano carbon material and monomers in the presence of a radical initiator.

With regard to the catalyst of the disclosure, in the catalytic reaction, C—C coupling reaction, the catalyst carrier and the transition metal element are added into the reaction system, so as to obtain the catalyst of the disclosure.

In the disclosure, the molecular weight of the polymer grafted onto the nano carbon materials is in a range from 300 to 100,000. Preferably, the molecular weight of the polymer grafted onto the nano carbon materials is in a range from 5,000 to 50,000.

In the catalyst of the disclosure, the transition metal element may be a metal complex, wherein the metal complex has a structure of formula (III):

$MX_pL_q$ (III), wherein M is transition metal element; X is a halogen, acetate, nitrate or cyanide; L is triphenylphosphine, trialkylphosphine, cyanogen, phenyl cyanide or 1,5-cyclooctadiene; and p and q are the same or different and are independently zero or an positive integer.

In the disclosure, the transition metal element may be nickel (Ni), rhodium (Rh), palladium (Pd) or platinum (Pt). Preferably, the transition metal element is Pd. In one embodiment, the metal complex is Pd(OAc)$_2$.

The catalyst of the disclosure can be used in the C—C coupling reaction, wherein the C—C coupling reaction can be a Heck coupling reaction, a Suzuki coupling reaction, a Stille coupling reaction or a Sonogashira coupling reaction.

The disclosure is described by, but not limited to, the following embodiments for illustrating the features and advantages of the disclosure.

The preparation of the catalyst carrier of the disclosure

Embodiment 1

2,2,6,6-tetramethylpiperidine-1-oxyl (TEMPO; 0.75 g; 4.8 mmol), benzoyl peroxide (BPO; 0.97 g; 4 mmol) and diphenyl(4-vinylphenyl)phosphine (DPVP; 8.6 g; 30 mmol) were added into a reaction flask (500 mL), and styrene (34.4 mL, 31.2 g, 300 mmol) and xylene (50 mL, deoxygenated) were added under a nitrogen atmosphere. The solution was under a vigorous stirring at 95° C. for 3 hours, and the color of the solution gradually turned to dark brown from orange red. The solution was then stirred at 130 for another 16 hours. After the solution was cooled down to room temperature, methanol (1000 mL, deoxygenated) was added to precipitate out the polymer. The solid was filtered and dried at 45 under vacuum overnight to afford a light yellow polymer powder (PDPVP; 28 g). GPC analysis of the polymer (as shown in FIG. 1) indicates that Mn=15400, and PDI=1.08.

Embodiment 2

Multi-wall Carbon Nanotubes (2.70 g; C$_{Tube}$-100, C$_{Tube}$-200, C$_{Tube}$-300, CNT Co., Ltd. KOREA) and the polymer (27.01 g) obtained in Embodiment 1 were added in a reaction flask. Xylene (100 mL, deoxygenated) was then added under a nitrogen atmosphere. The mixture was stirred at 130 for 24 hours. After the resulting mixture was cooled down to room temperature, THF (50 mL) was added to dilute the mixture, followed by filtration. The filtered solid was washed with THF for three times (50 mL), and dried under vacuum to obtain black powders (2.43 g; MWNT-PDPVP). TGA analysis of the product indicated that the amount of the polymer grafted onto the carbon tube was 28 wt %. In the ESCA analysis of the product (Electron Spectroscopy for Chemical Analysis), a signal of P$_{3p}$ (132 eV) indicates the product contains phosphorous atoms.

Embodiments 3-7

In Embodiments 3-7, the reactants (phenzyl halide (0.88 mmol; 1 equiv.), phenzylboronic acid (1.32 mmol; 1.5 equiv.)) according to Table 1 and the product MWNT-PDPVP (50 mg) of Embodiment 2, Pd(OAc)$_2$ (2 mg, 0.0088 mol, 1 mol %) and potassium carbonate (365 mg, 2.64 mmol) were added into a reaction flask, and then toluene (2 mL, deoxygenated) was added under a nitrogen atmosphere. The mixture was stirred at 110 for 1 hours. After cooling down to room temperature, the resulting mixture was subject to filtration, and the filtrate was analyzed by GC-MS. The conversion rate of the reagents, and the yields and structures of the products were shown in Table 1.

TABLE 1

| Embodiment | reactants | Conversion rate (%) | yield (%) | Structure | Molecular weight |
|---|---|---|---|---|---|
| 3 | bromobenzene | >99 | 99 | biphenyl | 154.1 |
| 4 | 4-bromotoluene | >99 | 96 | 4-methylbiphenyl | 168.1 |
| 5 | 4-bromobenzaldehyde | >99 | 96 | biphenyl-4-carbaldehyde | 196.1 |
| 6 | 4-bromoanisole | >99 | 96 | 4-methoxybiphenyl | 184.1 |
| 7 | 1-bromonaphthalene | >99 | 96 | 1-phenylnaphthalene | 204.1 |

Embodiment 8

MWNT-PDPVP (50 mg), 4'-bromo-acetophenone (175 mg; 0.88 mmol; 1 equiv.), phenylboronic acid (161 mg; 1.32 mmol; 1.5 equiv.), Pd(OAc)$_2$ (2 mg; 0.0088 mol; 1 mol %) and potassium carbonate (365 mg; 2.64 mmol) were added in a reaction flask, and then toluene (2 mL) was added under a nitrogen atmosphere. The mixture was stirred at 110 for 100 minutes. After cooling down to room temperature, the resulting mixture was subject to filtration, and the filtrate was analyzed by GC and ICP-MS. The results were shown in Table 2. The solids filtered out were washed with THF (15 mL×3), water and methanol (15 mL×3), and vacuum dried. The ESCA analysis of the resulting solids shows signals of $P_{3p}$ (134 eV) and $Pd_{3d5}$ (340 eV), indicating that the nano carbon tubes still contain phosphorous atoms and Pd metal.

Embodiments 9-15

Typical procedure: The catalyst recovered as in embodiment 8 was used (50 mg), 4'-bromo-acetophenone (175 mg; 0.88 mmol; 1 equiv.), phenylboronic acid (161 mg; 1.32 mmol; 1.5 equiv.) and potassium carbonate (365 mg; 2.64 mmol) were added into a reaction flask, and then toluene (2 mL) was added under a nitrogen atmosphere. The mixture was stirred at 110 for 100 minutes. After cooling down to room temperature, the resulting mixture was subject to filtration, and the filtrate was analyzed by GC and ICP-MS. The results were shown in Table 2.

TABLE 2

| Embodiment | Conversion rate (%) | Yield (%) | Leaching of Pd (%) |
|---|---|---|---|
| 8 | >99 | 99 | 0.2 |
| 9 | >99 | 99 | 0.4 |
| 10 | >99 | 99 | 0.3 |
| 11 | >99 | 96 | 0.3 |
| 12 | >99 | 89 | 0.3 |
| 13 | >99 | 91 | 0.4 |
| 14 | 94 | 78 | 0.3 |
| 15 | 90 | 79 | 0.2 |

Embodiment 16

MWNT-PDPVP (50 mg), phenyl halide listed in Table 3 (0.88 mmol, 1 equiv.), phenylboronic acid (161 mg; 1.32 mmol; 1.5 equiv.), Pd(OAc)$_2$ (2 mg; 0.0088 mol; 1 mol %) and potassium carbonate (365 mg; 2.64 mmol) were added into a reaction flask, and then toluene (2 mL) was added under a nitrogen atmosphere. The mixture was stirred at 110 for 100 minutes. After cooling down to room temperature, the resulting mixture was subject to filtration, and the filtrate was analyzed by GC. The results were shown in Table 3

TABLE 3

Catalytic results for different halides

| Embodiment | Phenyl halide | Conversion rate (%) | Yield (%) |
|---|---|---|---|
| 3 | bromobenzene (Ph-Br) | >99 | 99 |

TABLE 3-continued

Catalytic results for different halides

| | Phenyl halide | Conversion rate (%) | Yield (%) |
|---|---|---|---|
| Embodiment 16 | C6H5—I | >99 | 98 |

Embodiment 18

MWNT-PDPVP (210 mg) and Pd(OAc)$_2$ (10 mg) were added in a 50 mL Schlenk flask. Then THF (10 mL) was added into a reaction flask under a nitrogen atmosphere, and the mixture was stirred at room temperature overnight. The resulting mixture was subject to filtration. The resulting solid was washed with THF (15 mL×5), and dried under vacuum to obtain black powders (MWNT-PDPVP-Pd). The signals of $P_{3p}$ (135 eV) and $Pd_{3d5}$ (338 eV) in ESCA analysis indicates the powders containing phosphorous atoms and Pd metal.

Embodiment 19

Phenylbromide (137 mg, 0.88 mmol; 1 equiv.), phenylboronic acid (162 mg, 1.32 mmol; 1.5 equiv.), MWNT-PDPVP-Pd (50 mg) from Embodiment 18 and potassium carbonate (365 mg; 2.64 mmol) were added into a reaction flask, and then toluene (2 mL) was added under a nitrogen atmosphere. The mixture was stirred at 110 for 1 hr. After cooling down to room temperature, the resulting mixture was subject to filtration, and the filtrate was analyzed by GC (conversion >99%, yield 99%, leaching of Pd 0.3%).

In the disclosure, the metal are easily coordinated onto the polymer. Further, the polymer grafted on the nano carbon material, and the nano carbon material has high surface area and great mechanical strength, such that the catalyst of the disclosure is easy to be recovered. Moreover, the catalyst of the disclosure has great conversion rate and yield, and significantly eliminates the leaching of the metals from the carrier, so that the amount of the metal leaching into the product is minimal.

The disclosure has been described using exemplary preferred embodiments. However, it is to be understood that the scope of the disclosure is not limited to the disclosed arrangements. The scope of the claims, therefore, should be accorded the broadest interpretation, so as to encompass all such modifications and similar arrangements.

The invention claimed is:

1. A catalyst carrier, comprising:
a nano carbon material; and a polymer grafted on the nano carbon material, wherein the polymer has a repetitive unit comprising a phosphorous atom, and wherein the polymer further comprises polymeric vinyl-based monomers.

2. The catalyst carrier of claim 1, wherein the nano carbon material is at least one selected from the group consisting of a single-layer carbon nano-tube, a multilayer carbon nano-tube, a nano carbon fiber, a nano carbon ball, an active carbon and a carbon black.

3. The catalyst carrier of claim 1, wherein a main chain of the polymer has an end group grafted on the nano carbon material.

4. The catalyst carrier of claim 1, wherein the repetitive unit has a structure of formula (I):

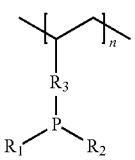

(I)

wherein $R_1$ and $R_2$ are independently selected from the group consisting of $C_1$-$C_{10}$alkyl, $C_3$-$C_8$cycloalkyl, $C_6$-$C_{10}$aryl, $C_1$-$C_4$alkyl or $C_2$-$C_4$alkenyl substituted $C_6$-$C_{10}$aryl and $C_6$-$C_{10}$-heteroaryl;

$R_3$ is one selected from the group consisting of $C_1$-$C_{10}$alkylene, $C_3$-$C_8$cycloalkylene, $C_3$-$C_8$cycloalkylene or $C_6$-$C_{12}$arylene having a carbon atom bound to P and substituted with a hetero atom, $C_6$-$C_{12}$arylene, a halo substituted $C_6$-$C_{12}$arylene, fused $C_6$-$C_{12}$arylene, fused $C_6$-$C_{12}$arylene substituted with $C_6$-$C_{12}$aryl and a metal complex having cyclo-olefins as ligands, in which one of the cyclo-olefins is bound to the main chain of the polymer and bound to P;

P is phosphorous; and n is a positive integer.

5. The catalyst carrier of claim 4, wherein the repetitive unit has a structure of one of formulae (Ia) to (Ih):

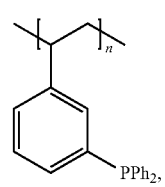

(Ia)

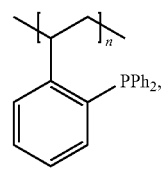

(Ib)

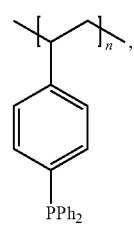

(Ic)

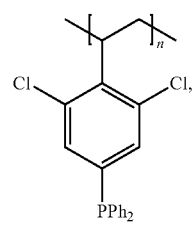

(Id)

-continued

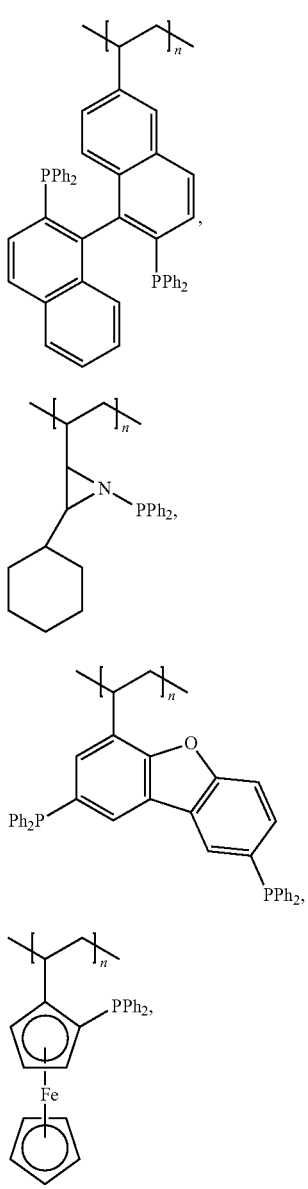

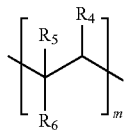

wherein Ph is phenyl; and n is a positive integer.

6. The catalyst carrier of claim 1, wherein the repetitive unit comprised of polymeric vinyl-based monomers has a structure of formula (II):

(II)

wherein $R_4$ and $R_6$ are independently selected from the group consisting of H, ester, $C_1$-$C_{10}$alkyl, $C_2$-$C_8$alkene, $C_3$-$C_8$cycloalkyl, 4- to 8-membered heterocycloalkyl and $C_6$-$C_{10}$aryl;
$R_5$ is H or $C_1$-$C_{10}$alkyl; and
m is a positive integer.

7. The catalyst carrier of claim 1, wherein the polymer has a structure of formula (IV):

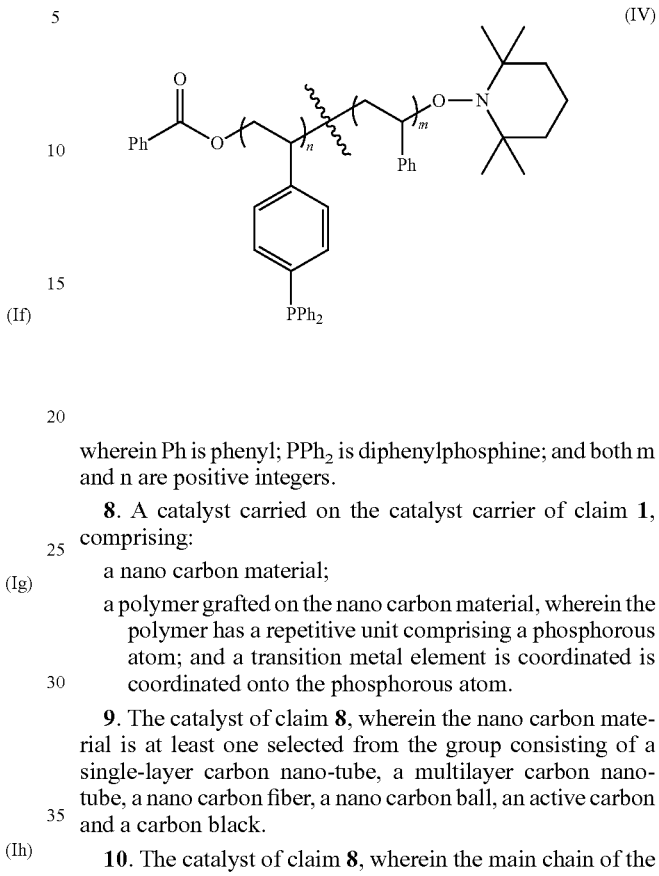

wherein Ph is phenyl; $PPh_2$ is diphenylphosphine; and both m and n are positive integers.

8. A catalyst carried on the catalyst carrier of claim 1, comprising:
a nano carbon material;
a polymer grafted on the nano carbon material, wherein the polymer has a repetitive unit comprising a phosphorous atom; and a transition metal element is coordinated is coordinated onto the phosphorous atom.

9. The catalyst of claim 8, wherein the nano carbon material is at least one selected from the group consisting of a single-layer carbon nano-tube, a multilayer carbon nano-tube, a nano carbon fiber, a nano carbon ball, an active carbon and a carbon black.

10. The catalyst of claim 8, wherein the main chain of the polymer has an end group grafted on the nano carbon material.

11. The catalyst of claim 8, wherein the repetitive unit has a structure of formula (I):

wherein $R_1$ and $R_2$ are independently selected from the group consisting of $C_1$-$C_{10}$alkyl, $C_3$-$C_8$cycloalkyl, $C_6$-$C_{10}$aryl, $C_1$-$C_4$alkyl or $C_2$-$C_4$alkenyl substituted $C_6$-$C_{10}$aryl and $C_6$-$C_{10}$heteroaryl;
$R_3$ is one selected from the group consisting of $C_1$-$C_{10}$alkylene, $C_3$-$C_8$cycloalkylene, $C_3$-$C_8$cycloalkylene or $C_6$-$C_{12}$arylene having a carbon atom bound to P and substituted with a hetero atom, $C_6$-$C_{12}$arylene, a halo substituted $C_6$-$C_{12}$arylene, fused $C_6$-$C_{12}$arylene, fused $C_6$-$C_{12}$arylene substituted with $C_6$-$C_{12}$aryl, and a metal complex having cyclo-olefins as ligands, in which one of the cyclo-olefins is bound to the main chain of the polymer and bound to P;

P is a phosphorous; and n is a positive integer.

12. The catalyst of claim 11, wherein the repetitive unit has a structure of one of formulae (Ia) to (Ih):

(Ia)
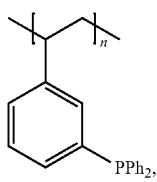

(Ib)
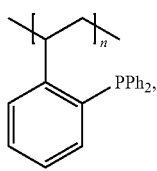

(Ic)
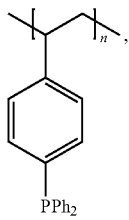

(Id)
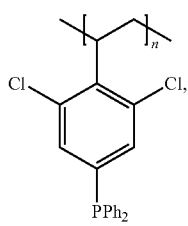

(Ie)
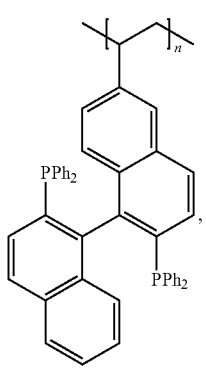

(If)
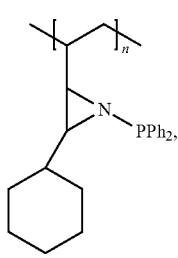

-continued

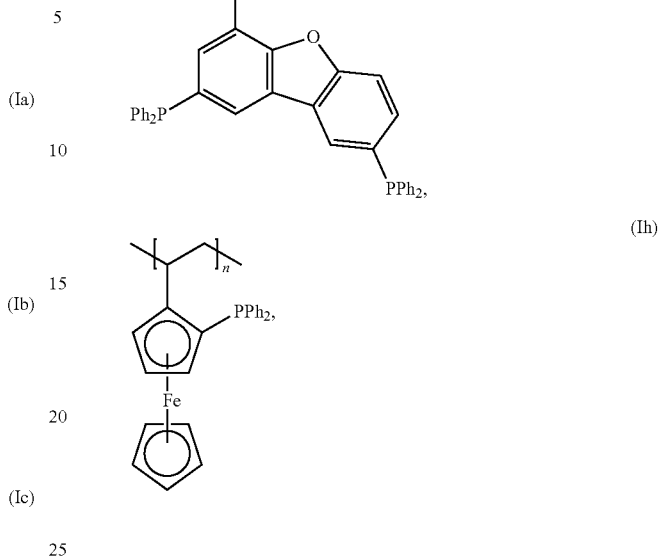

(Ig)

(Ih)

wherein P is phosphorous; Ph is phenyl; and n is a positive integer.

13. The catalyst of claim 8, wherein the polymer further comprises polymeric vinyl-based monomers.

14. The catalyst of claim 13, wherein the repetitive unit comprised of polymeric vinyl-based monomers has a structure of formula (II):

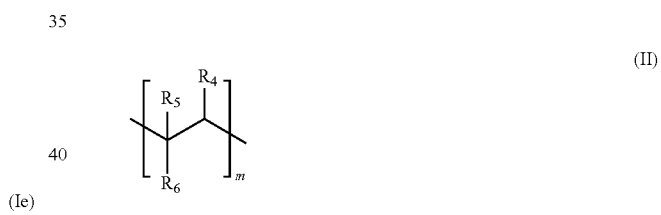

(II)

wherein $R_4$ and $R_6$ are independently selected from the group consisting of H, ester, $C_1$-$C_{10}$alkyl, $C_2$-$C_8$alkene, $C_3$-$C_8$cycloalkyl, 4- to 8-membered heterocycloalkyl and $C_6$-$C_{10}$aryl;

$R_5$ is H or $C_1$-$C_{10}$alkyl; and m is a positive integer.

15. The catalyst of claim 8, wherein the transition metal element provided from a metal complex.

16. The catalyst of claim 15, wherein the metal complex has a structure of formula (III):

$$MX_pL_q \quad \text{(III),}$$

wherein M is one of nickel, rhodium, palladium and platinum;

X is a halogen, acetate, nitrate or cyanide;

L is triphenylphosphine, trialkylphosphine, cyano, phenyl cyanide or 1,5-cyclooctadiene; and p and q are independently zero or an positive integer.

17. The catalyst of claim 8, wherein the polymer has a structure of formula (IV):

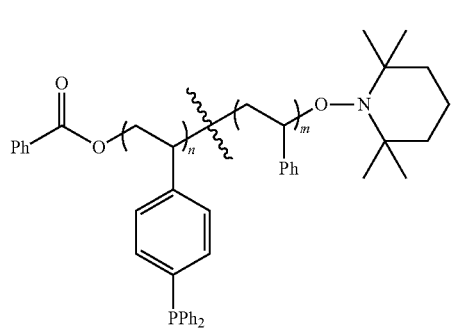
(IV)
wherein Ph is phenyl; PPh$_2$ is diphenylphosphine; and both m and n are positive integers.
18. A method for performing a C—C coupling reaction, comprising the step of using the catalyst of one of claims 8 to 17.